(12) United States Patent
Borenstein et al.

(10) Patent No.: US 9,180,239 B2
(45) Date of Patent: Nov. 10, 2015

(54) METHODS FOR REDUCING THE BLOOD PRIMING VOLUME AND MEMBRANE SURFACE AREA IN MICROFLUIDIC LUNG ASSIST DEVICES

(71) Applicant: The Charles Stark Draper Laboratory, Inc., Cambridge, MA (US)

(72) Inventors: Jeffrey T. Borenstein, Newton, MA (US); Joseph L. Charest, Cambridge, MA (US); James C. Hsiao, Watertown, MA (US); Tatiana Kniazeva, Boston, MA (US); Ernest S. Kim, Cambridge, MA (US); Alla Epshteyn, Brookline, MA (US); Vijaya Kolachalama, Cambridge, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 33 days.

(21) Appl. No.: 13/705,795

(22) Filed: Dec. 5, 2012

(65) Prior Publication Data

US 2013/0144266 A1 Jun. 6, 2013

Related U.S. Application Data

(60) Provisional application No. 61/567,104, filed on Dec. 5, 2011.

(51) Int. Cl.
*A61M 1/16* (2006.01)

(52) U.S. Cl.
CPC ......... *A61M 1/1698* (2013.01); *A61M 2206/20* (2013.01)

(58) Field of Classification Search
CPC ....... A61M 1/14; A61M 1/16; A61M 1/1698; A61M 1/32; A61M 2206/20; B01D 63/082; B01D 63/088; B01D 2313/08; B01D 2313/38
USPC .................................. 604/6.14; 422/44–48
See application file for complete search history.

(56) References Cited

U.S. PATENT DOCUMENTS

| | | | |
|---|---|---|---|
| 2,876,769 A | 3/1959 | Cordova | |
| 3,489,647 A | 1/1970 | Kolobow | |

(Continued)

FOREIGN PATENT DOCUMENTS

| | | |
|---|---|---|
| DE | 10 2008 045 621 A1 | 3/2010 |
| EP | 0 416 92 | 12/1981 |

(Continued)

OTHER PUBLICATIONS

Alex C. M. Kuo, Poly(dimethylsiloxane), Polymer data handbook, 1999 Oxford University Press, Inc.

(Continued)

*Primary Examiner* — Philip R Wiest
*Assistant Examiner* — Benjamin Klein
(74) *Attorney, Agent, or Firm* — Edward A. Gordon; Foley & Lardner LLP

(57) ABSTRACT

A device and method for oxygenating blood is disclosed herein. The device includes a plurality of passive mixing elements that causes a fluid to mix as it flows through the device. The passive mixing elements continually expose new red blood cells to the portion of the flow channel where oxygenation can occur. Accordingly, in some implementations, the device and method uses less blood to prime the device and allows for the oxygenation of blood with a substantial shorter flow channel when compared to conventional oxygenation methods and devices.

19 Claims, 10 Drawing Sheets

(56) References Cited

U.S. PATENT DOCUMENTS

| | | | |
|---|---|---|---|
| 3,738,813 A | | 6/1973 | Esmond |
| 3,847,211 A | | 11/1974 | Fischel et al. |
| 4,620,965 A | | 11/1986 | Fukusawa et al. |
| 4,756,835 A | | 7/1988 | Wilson |
| 4,997,565 A | * | 3/1991 | Niesen ............... 210/321.84 |
| 5,120,445 A | * | 6/1992 | Colman ................ 210/640 |
| 5,207,639 A | | 5/1993 | Cooper |
| 5,254,259 A | * | 10/1993 | Bellhouse et al. ........... 210/650 |
| 6,241,945 B1 | | 6/2001 | Owen |
| 6,514,412 B1 | * | 2/2003 | Insley et al. ............... 210/649 |
| 6,602,468 B2 | | 8/2003 | Patterson et al. |
| 7,713,544 B2 | | 5/2010 | Chaikof et al. |
| 7,759,113 B2 | | 7/2010 | Vacanti et al. |
| 7,955,504 B1 | * | 6/2011 | Jovanovic et al. ....... 210/321.71 |
| 8,128,822 B2 | | 3/2012 | Browning et al. |
| 8,137,554 B2 | | 3/2012 | Jovanovic et al. |
| 8,266,791 B2 | | 9/2012 | Borenstein et al. |
| 2002/0182241 A1 | | 12/2002 | Borenstein et al. |
| 2003/0121841 A1 | | 7/2003 | Harttig et al. |
| 2003/0175149 A1 | | 9/2003 | Searles et al. |
| 2005/0202557 A1 | | 9/2005 | Borenstein et al. |
| 2006/0136182 A1 | | 6/2006 | Vacanti et al. |
| 2006/0173394 A1 | | 8/2006 | Stroock et al. |
| 2007/0119771 A1 | | 5/2007 | Schukar et al. |
| 2008/0093298 A1 | | 4/2008 | Browning et al. |
| 2009/0081079 A1 | * | 3/2009 | Johns ............................ 422/46 |
| 2009/0234332 A1 | | 9/2009 | Borenstein et al. |
| 2010/0098742 A1 | | 4/2010 | Vacanti et al. |
| 2010/0118642 A1 | * | 5/2010 | Ho et al. ....................... 366/336 |
| 2010/0267136 A1 | | 10/2010 | Vacanti et al. |
| 2011/0158847 A1 | | 6/2011 | Charest et al. |
| 2011/0186165 A1 | | 8/2011 | Borenstein et al. |
| 2011/0226686 A1 | * | 9/2011 | Maurer ......................... 210/206 |
| 2012/0182609 A1 | | 7/2012 | Borenstein et al. |

FOREIGN PATENT DOCUMENTS

| | | |
|---|---|---|
| GB | 1 408 562 | 10/1975 |
| JP | 62-064372 | 3/1987 |
| JP | 2003-093853 | 4/2003 |
| WO | WO-02/076529 | 10/2002 |
| WO | WO-2006/042079 A1 | 4/2006 |
| WO | WO-2010/025926 | 3/2010 |
| WO | WO-2011/150216 | 12/2011 |
| WO | WO-2011/150216 A1 | 12/2011 |

OTHER PUBLICATIONS

Burgess, K. et al., "Towards microfabricated biohybrid artificial lung modules for chronic respiratory support," Biomedical Microdevices, vol. 11, No. 12 Aug. 2008, pp. 117-127.

International Preliminary Report on Patentability dated Dec. 6, 2012, International application No. PCT/US2011/038148, International filing date May 26, 2011.
International Search Report and Written Opinion, International application No. PCT/US2012/067971, International filing date Dec. 5, 2012.
International Search Report, International Application No. PCT/US2010/062537, International Filing Date Dec. 30, 2010.
International Preliminary Report on Patentability mailed Jul. 12, 2012, International application No. PCT/US2010/062537, International filing date Dec. 30, 2010.
US Notice of Allowance in U.S. Appl. No. 13/116,219 DTD Jun. 14, 2013.
US Office Action in U.S. Appl. No. 12/981,903 DTD Feb. 22, 2013.
US Office Action in U.S. Appl. No. 12/981,903 DTD Aug. 30, 2012.
International Preliminary Report on Patentability mailed on Jun. 19, 2014 in PCT Application No. PCT/US2012/067971.
Stroock, et al., "Chaotic Mixer for Microchannels", Science, vol. 295, pp. 647-651, Jan. 25, 2002.
US Office Action in U.S. Appl. No. 12/981,903 dated Jul. 30, 2014.
Wu et al., "Construction of Microfluidic Chips Using Polydimethylsiloxane for Adhesive Bonding," Lab on a Chip, 5:1393-1398 (2005).
First Office Action issued in Australian Patent Application No. 2010339409 dated Sep. 29, 2014.
First Office Action issued on Jul. 17, 2014 in Chinese Patent Application No. 2011800367123.
Office Action issued Dec. 4, 2014 in Japanese Patent Application No. 2012-547304.
Patent Examination Report No. 1 in Australian Patent Application No. 2011258203, dated Nov. 4, 2014.
US Notice of Allowance in U.S. Appl. No. 12/981,903 DTD Feb. 2, 2015.
Borenstein et al., "Microfabrication Technology for Vascularized Tissue Engineering," Biomedical Microdevices, 4(3):167-175 (2002).
Hongkai et al., "Construction of Microfluidic Chips Using Polydimethylsiloxane for Adhesive Bonding," Lab on a Chip, 5:1393-1398 (2005).
International Search Report in PCT/US2011/038148, dated Aug. 26, 2011.
Leclerc et al., "Cell Culture in 3-Dimensional Microfluidic Structure of PDMS (polydimethylsiloxane)," Biomedical Microdevices, 5(2):109-114 (2003).
Office Action in U.S. Appl. No. 12/981,903 dated Sep. 11, 2013.
Yasuda, H. "Units of Gas Permeability Constants", Journal of Applied Polymer Science, 1975, vol. 19, pp. 2529-2536.
Notice of Allowance in U.S. Appl. No. 13/116,219 dated Oct. 4, 2013.
Office Action issued Mar. 26, 2015 in Japanese Patent Application No. 2013-512244.
International Search Report and Written Opinion mailed Jul. 17, 2015 in PCT Application No. PCT/US2015/027321.

* cited by examiner

A)

B)

C)

D)

E)

F)

G)

H)

METHODS FOR REDUCING THE BLOOD PRIMING VOLUME AND MEMBRANE SURFACE AREA IN MICROFLUIDIC LUNG ASSIST DEVICES

CROSS-REFERENCE TO RELATED PATENT APPLICATIONS

This application claims priority from Provisional U.S. Patent Application 61/567,104, filed Dec. 5, 2011, incorporated herein by reference in its entirety.

GOVERNMENT LICENSE RIGHTS

This invention was made with government support under Grant No. R21HL106585 awarded by the National Institutes of Health. The government has certain rights in the invention.

BACKGROUND OF THE DISCLOSURE

Blood oxygenation systems are used for short term respiratory support, such as during coronary artery bypass graft surgeries or for acute respiratory distress syndrome patients. In current systems, blood is oxygenated by pumping oxygen through an inner, hollow fiber pumping blood though a larger, outer fiber that encapsulates the inner fiber. The walls of the inner fiber are permeable to oxygen and allow for the oxygenation of blood near the inner fiber. Current oxygenation systems maintain a laminar blood flow, only allowing the oxygenation of red blood cells within a close proximity of the permeable membrane.

SUMMARY OF THE DISCLOSURE

According to one aspect of the disclosure, a microfluidic oxygenation device includes a first polymer layer defining a first oxygen flow channel. The device also includes a second polymer layer defining a first blood flow channel. The first blood flow channel overlaps the first oxygen flow channel, and the two channels are separated by a permeable membrane that allows communication between the channels at overlapping portions. Additionally, first blood flow channel further includes at least one passive mixing element along at least one wall. The passive mixing element is configured to redistribute a fluid flowing through the first blood flow channel within the channel.

In some implementations, the passive mixing element is one of a straight ridge, an angled ridge, a chevron canal, a dome, a cone, a pit or a post. In some implementations, a first fluid, such as oxygen, flows through the first oxygen flow channel and a second fluid, such as blood, flows through the first blood flow channel.

In some implementations, the height or depth of the passive mixing element is less than about 30% of the height of the first blood flow channel, and the passive mixing elements are incorporated into the floor of the first blood flow channel. In other implementations, the height of the first blood flow channel is between about 10 and 100 microns and the membrane thickness is between about 10 and about 50 microns. In yet other implementations, the length of the first oxygen flow channel and the first blood flow channel is between about 1 mm and 50 mm and the width is between about 100 microns and 200 microns.

In other implementations, the membrane is permeable to oxygen and carbon dioxide. In yet other implementations, the walls of the first blood flow channel are coated with an anticoagulant. In yet other implementations, the device includes a second blood flow channel separated from the first oxygen flow channel by a second permeable membrane.

According to another aspect of the disclosure, a method for oxygenating deoxygenate blood includes providing a microfluidic device comprising a first polymer layer defining a first oxygen flow channel and a second polymer layer defining a first blood flow channel. The first blood flow channel also includes at least one passive mixing element. A membrane separates the first oxygen flow channel and the first blood flow channel and allows communication between the first oxygen flow channel and the first blood flow channel. The method also includes introducing partially deoxygenated blood into a proximal end of the microfluidic device, and flowing the partially deoxygenated blood through the device. Additionally, the method includes flowing oxygen through the first oxygen flow channel. Finally, oxygenated blood is received at a distal end of the microfluidic device.

In some implementations, the method also includes collecting partially deoxygenated blood from a patient, flowing the partially deoxygenated blood through the first blood flow channel to reoxygenate the blood, and returning the reoxygenated blood to the patient. In other implementations, the method further includes removing carbon dioxide from the partially deoxygenated blood as the partially deoxygenated blood flows through the first blood flow channel.

In yet other implementations, the method also includes flowing oxygen through the first oxygen flow channel from a first direction, and flowing blood through the first blood flow channel in a second direction opposite to the first direction. In some implementations, the blood is flowed through the first blood flow channel at 4-5 L/min and oxygen is transferred to the blood at a rate of about 150-200 mL/min.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

Figure 1:
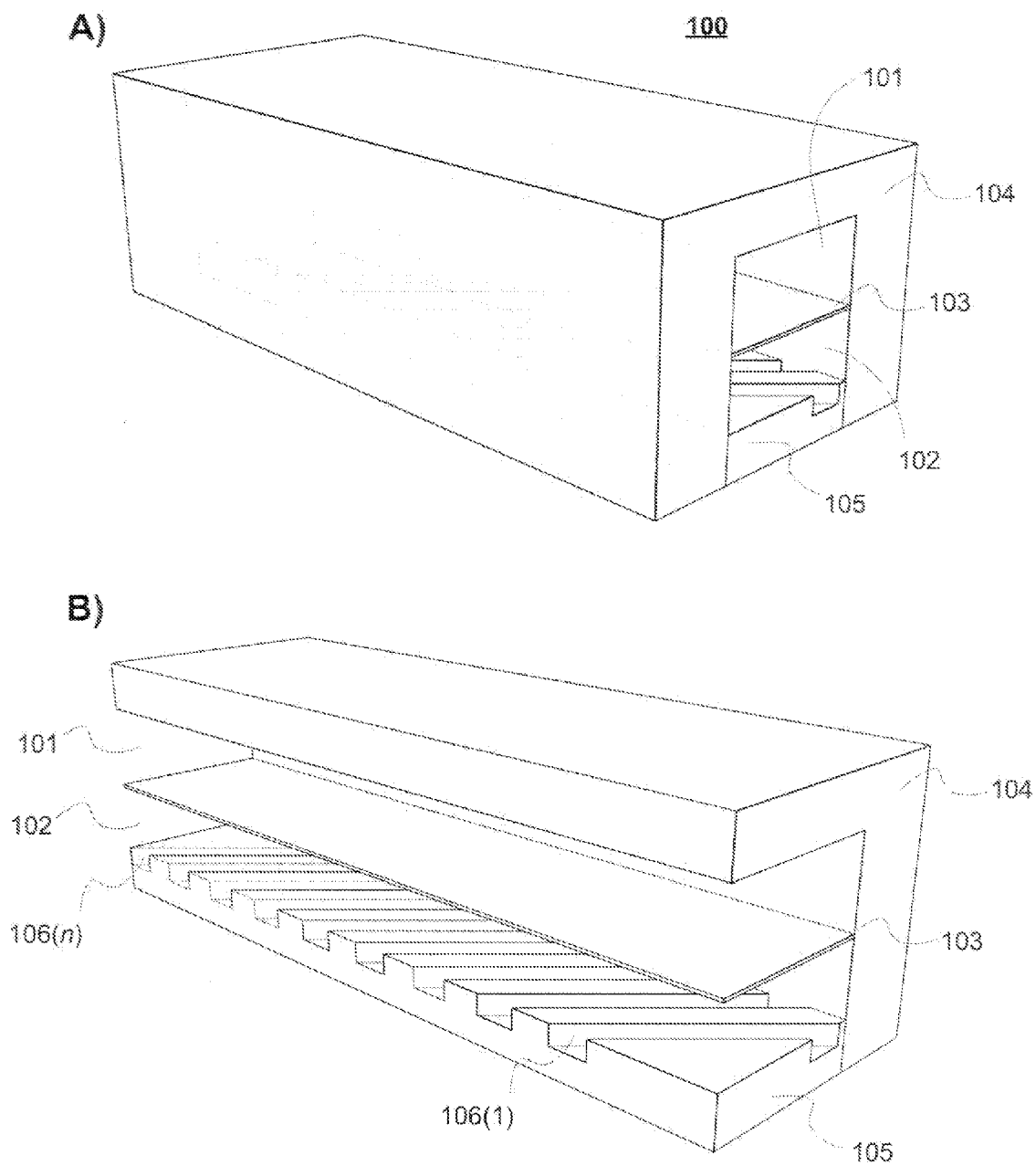
FIG. 1A is an isometric view of a device for oxygenating blood, according to one illustrative implementation of the present disclosure.
FIG. 1B is a cut-away view of a device for oxygenating blood, according to one illustrative implementation of the present disclosure.
FIG. 1C is an end view of a device of oxygenating blood as depicted in FIG. 1, according to one illustrative implementation of the present disclosure.
Figure 1:
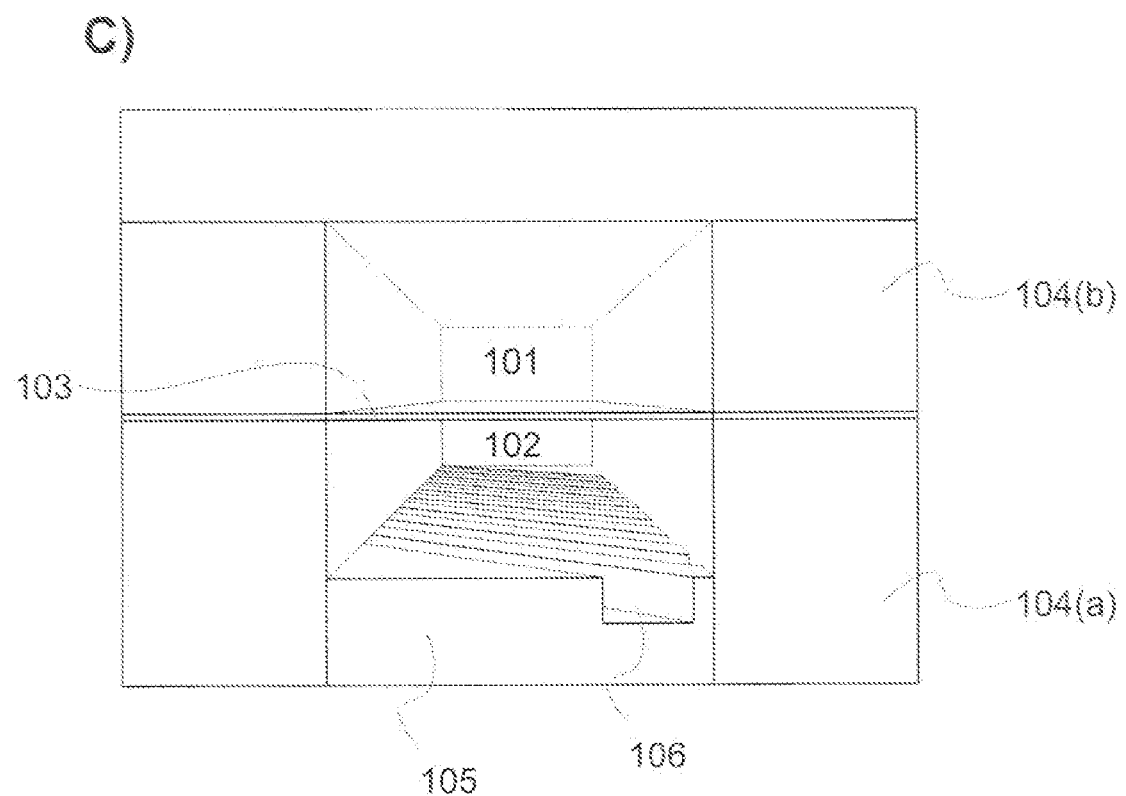

The various concepts introduced above and discussed in greater detail below may be implemented in any of numerous ways, as the described concepts are not limited to any particular manner of implementation. Examples of specific implementations and applications are provided primarily for illustrative purposes.

The present system described herein generally relates to a system and method for oxygenating blood. Accordingly, in various implementations, the disclosure relates to oxygenating blood by passively mixing the blood as it flows through the blood oxygenation device. In certain implementations, the device includes a plurality of passive elements on one wall of the device to mix the flowing blood.

FIGS. 1A and 1B show an isometric view of a blood oxygenation device 100 and a cutaway view thereof. Described in greater detail below, but briefly, the device 100 includes a first flow channel 101 separated from a second flow channel 102 by a gas permeable membrane 103. The floor 105 of the second flow channel 102 includes a passive mixing element 106. The flow channels 101 and 102 are fabricated within a polymer substrate 104.

As illustrated in FIGS. 1A and 1B and discussed above, device 100 includes a first flow channel 101 and second flow channel 102 fabricated within a polymer substrate 104. In some implementations, the polymer substrate 104 is a thermoplastic, such as polystyrene or polyimide, biodegradable polyesters, such as polycaprolactone (PCL), or soft elastomers such as polyglycerol sebacate (PGS). In other implementations, the substrate 104 is polydimethylsiloxane (PDMS), poly(N-isopropylacrylamide). In yet other implementations, the substrate 104 includes non-polymer materials such as, but not limited to, ceramics; metals; glasses; nanotubes or nanowires formed from, for example, carbon or zinc oxide; or other non-polymer materials.

In some implementations, the device 100 and the passive mixing elements 106 are fabricated in the substrate 104 using, for example, photolithographic techniques, injection molding, direct micromachining, deep RIE etching, hot embossing, or any combinations thereof.

The first flow channel 101 communicates with the second flow channel 102 via the membrane 103. In some implementations, the membrane 103 is permeable or semi-permeable to ions, molecules, cells or any combination thereof. For example, the membrane 103 may allow for oxygen to pass from the first flow channel 101 to the second flow channel 102 and carbon dioxide to pass from the second flow channel 102 to the first flow channel 101. However, in some implementations, the membrane 103 is not permeable to red blood cells. In some implementations, the membrane 103 is fabricated from a semi-porous or porous material, such as polyethersulfone or PDMS. In other implementations, the membrane 103 is created by electrospinning a polymer to create a flexible, porous polymer mesh.

The first flow channel 101 and the second flow channel 102 of device 100 run substantially parallel to one another, and, as described above, are separated by the membrane 103 at overlapping portions. In some implementations, the first flow channel 101 includes three smooth walls, with the fourth wall being the membrane 103. In other implementations, the device 100 includes additional flow channels to the left, right, and/or above the first flow channel 101. In some of these implementations the first flow channel 101 is also separated from these additional flow channels by a permeable membrane 103. In other implementations, the first flow channel is configured for the flow of a gas. For example, oxygen may be flowed through the first flow channel 101. In other implementations, the first flow channel 101 is configured to flow a liquid. For example, the flow first flow channel may be configured to flow blood.

The second flow channel 102 includes at least one passive mixing element 106 along at least one wall of the channel. In the implementation of device 100, the floor 105 includes passive mixing elements 106(1)-106($n$). In other implementations, any wall of the first or second flow channel can include a passive mixing element 106. In some implementations, the floor, or other wall(s) that include a passive mixing element 106, is replaceable, such that different configurations of passive mixing elements can be used for different fluids. In yet other implementations the device 100, or components thereof, is disposable.

As described below, in some implementations, the passive mixing elements include a plurality of ridges, channels, protrusions, or any combination thereof. In some implementations the passive mixing elements 106(1)-106($n$) span the entire length of a flow channel. In other implementations, the mixing elements 106 cover only a sub-portion of the total length of a flow channel 102. In yet other implementations, the passive mixing elements 106(1)-106($n$) are grouped together. For example, the fluid flow channel 102 may contain a first type of passive mixing element 106 along a first portion of the flow channel 102 and then a second type of passive mixing element 106 along a second portion of the flow channel 102.

FIG. 1C illustrates an end view of device 100. In some implementations, the device 100 is fabricated as a top component 104($b$) and a bottom component 104($b$) that are fabricated separately and assembled to form device 100. In some implementations, the components 104($a$), 104($b$), and the membrane 103 are attached to one another with an adhesive. For example, the components of device 100 can be bound together with a chemical adhesive, plasma bonding, and/or by clamping the components together. In other implementations, the device 100 is fabricated as a single, continuous unit. For example, device 100 can be created by injection molding. In yet other implementations, the top portion 104($b$) and the bottom portion 104($a$) are formed by injection molding. In some implementations, after the device 100 is fabricated the channels are coated with an anticoagulant. In other implementations, the anticoagulant is embedded in the polymer substrate 104.

In some implementations the height or depth of a passive mixing element 106 is between about 5% and about 10%, between about 10% and about 20%, or between about 20% and 30% of the total height of the flow channel 102. In some implementations, each passive mixing element in a channel is the same height or depth. While in other implementations, the height or depth of the passive mixing elements changes along the length of the flow channel 102.

In some implementations, the width, height, and length of the first flow channel 101 and second flow channel 102 are the same. In other implementations, one or all of the dimensions between different flow channels is different. In some implementations, the height of the flow channels is between about 10 microns and 25 microns, between about 25 microns and 50 microns, or between about 50 microns and 100 microns. In some implementations the thickness of the membrane 103 is between about 10 microns and 25 microns, between about 25 microns and 50 microns, or between about 50 microns and 100 microns. In some implementations, the length of the flow channels is between about 1 mm and 10 mm, between about 10 mm and 50 mm, or between about 50 mm and 100 mm and the width is between about 100 microns and 200 microns, between 200 microns and 500 microns, or between about 500 microns and 1 cm.

Figure 2:
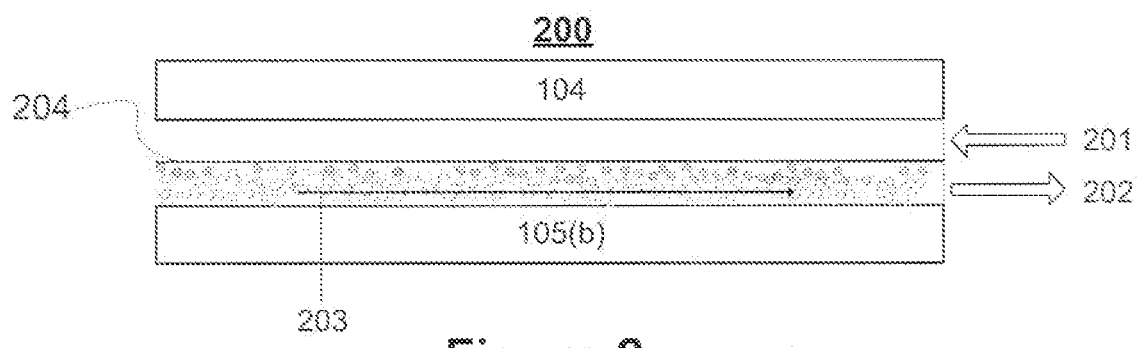
FIG. 2 is a cross-sectional view illustrating the flow patterns of blood in a blood oxygenation device without passive mixing elements, according to one illustrative implementation of the present disclosure.

FIG. 2 illustrates how fluid may flow through a blood oxygenation device without passive mixing elements similar. FIG. 2 illustrates a blood oxygenation device 201 without passive mixing elements along the floor 105(b). In this example, oxygen flows through the first flow channel 201 as deoxygenated blood (white circles) flows through the second flow channel 202. The blood in the second flow channel 201 flows in a laminar pattern 203. The blood cells become oxygenated (gray circles) as they flow substantially close to the membrane 204. In some implementations, because oxygen diffusion can only occur at distances substantially close to the membrane 204, the portion of blood flowing along the floor of the second flow channel 202 may never become oxygenated.

Figure 3:
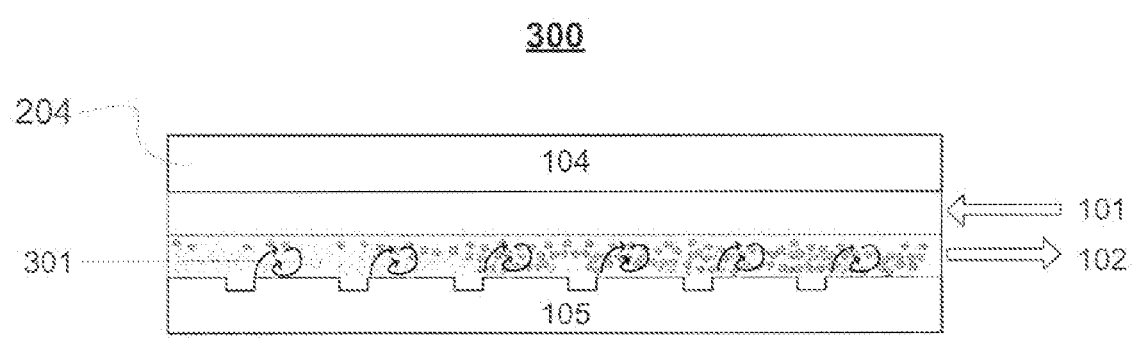
FIG. 3 is a cross-sectional view illustrating the flow patterns of blood in a blood oxygenation device with passive mixing elements as depicted in FIGS. 1A-1C, according to one illustrative implementation of the present disclosure.

In contrast, FIG. 3 illustrates how blood flows through a blood oxygenation device 300 similar to the blood oxygenation device 100. The floor 105 of device 300 includes a number of passive flow elements 106. These passive flow elements 106 create non-laminar flow 301 in the fluid of channel 102. In some implementations this creates chaotic flow in channel 102. For example, in some implementations, the passive mixing elements 106 drive fluid from the bottom of the fluid flow channel 102 towards the membrane 103. In some implementations, the passive mixing elements 106 create a rotational flow within in the flow channel. For example, the passive mixing elements 106 may create a rifling effect that causes the fluid to swirl as it flows down the flow channel 102. In some implementations, the device 100 induces mixing within a fluid without inducing mechanical trauma to the components of the fluid. For example, the passive mixing elements 106 of device 100 may drive blood towards the membrane 103 without causing the red blood cells to hemorrhage or clot.

As illustrated in FIG. 3, the device 300, with the passive mixing elements 106, is able to fully oxygenate the blood over a shorter span of the device's length when compared to device 200 that does not include a passive mixing element 106. This allows for a shorter channel, and therefore allows the device to be primed with less blood than a channel without such passive mixing elements.

Figure 4:
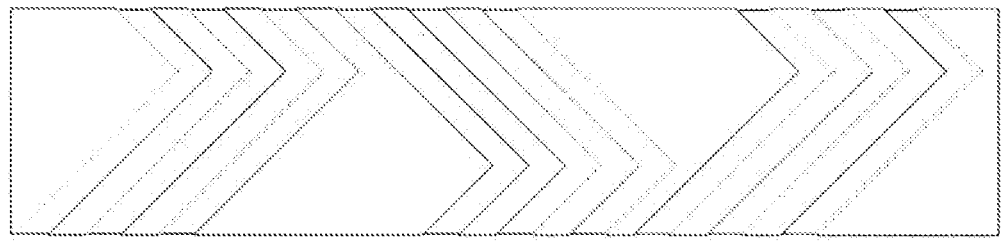
FIGS. 4A-J are top and isometric view of exemplary passive mixing elements of a blood oxygenation device as depicted in FIG. 1, in accordance with an illustrative implementation of the present disclosure.
Figure 4:
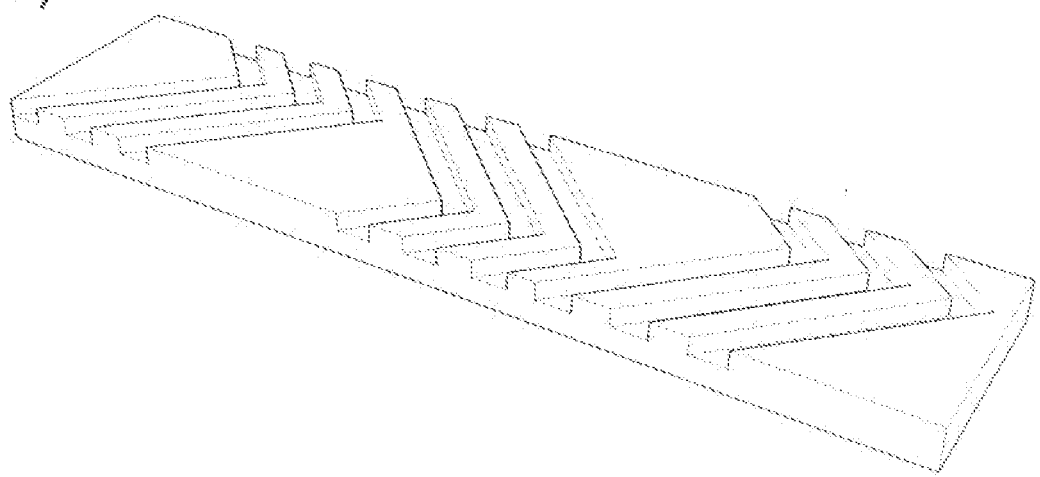
Figure 4:
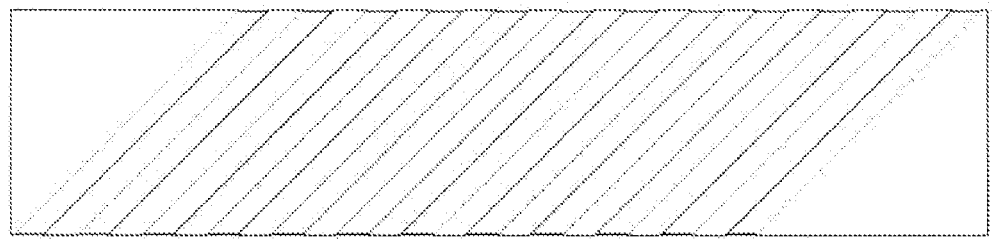
Figure 4:
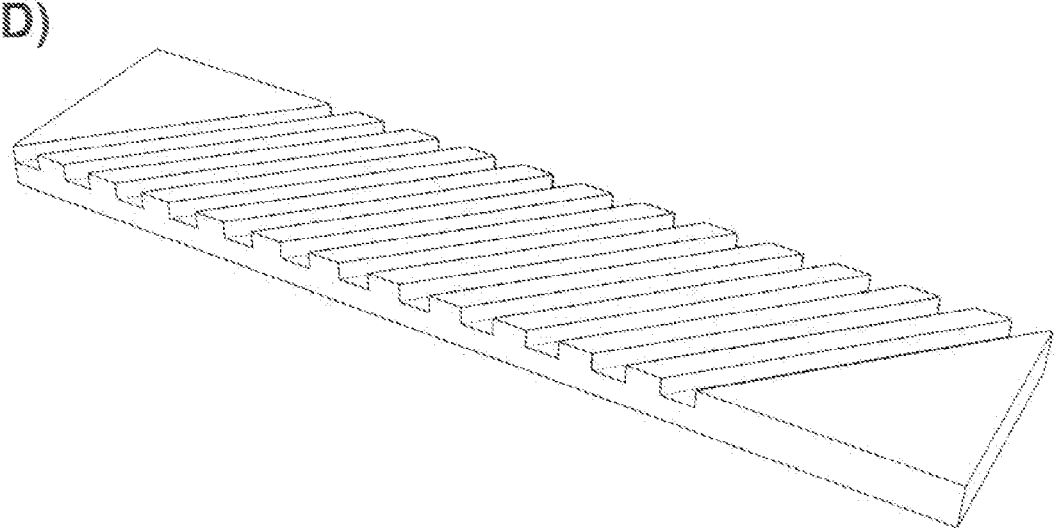
Figure 4:
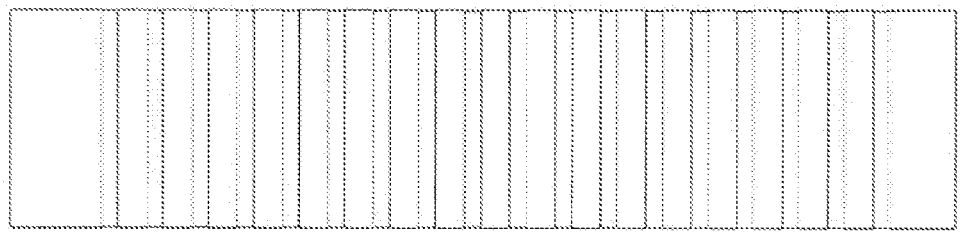
Figure 4:
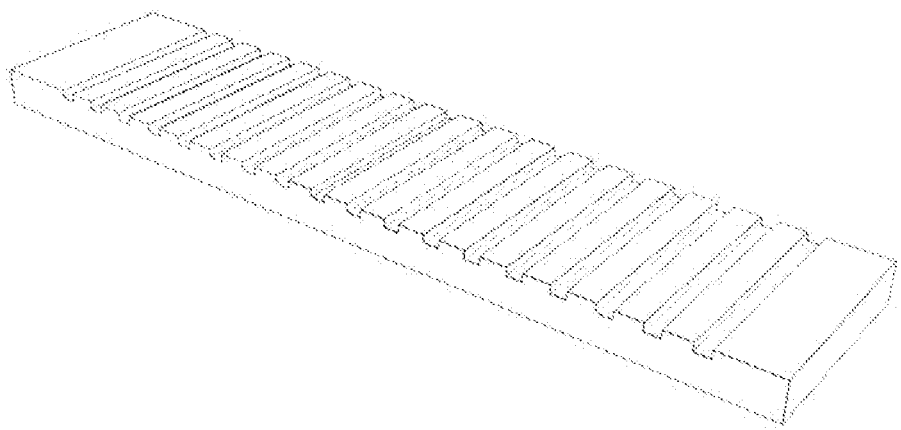
Figure 4:
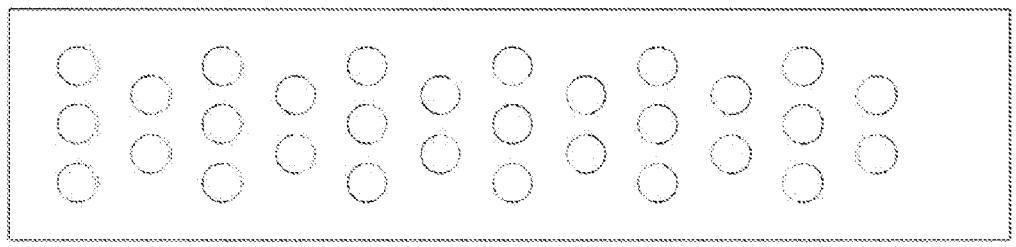
Figure 4:
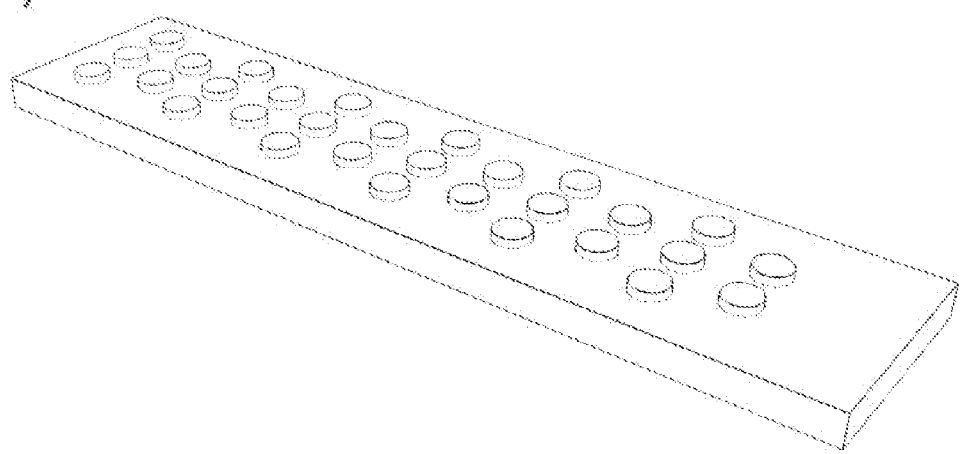
Figure 4:
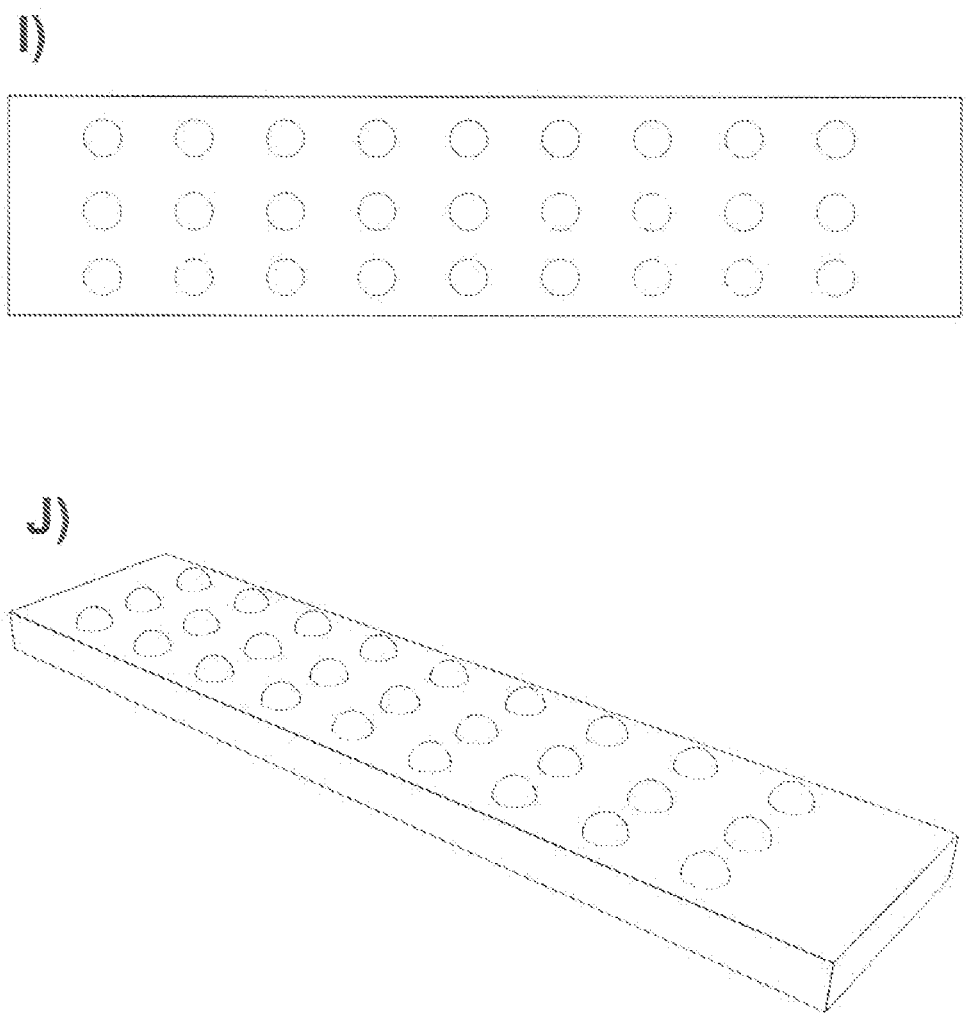

FIGS. 4A-J show a top and isometric view of possible, non-limiting examples of passive mixing elements 106. FIGS. 4A and 4B illustrate an alternating herringbone pattern. The design consists of a herringbone pattern wherein the center of the herringbone pattern shifts from one side of the flow channel to the other through the length of the flow channel 102. In some implementations, the alternating herringbone pattern causes the fluid in the flow channel to enter the flow channel and begin rotating in a first direction. Then, when the flowing fluid encounters a shifted herringbone pattern, the fluid is forced to rotate in a direction opposite to the first rotational direction. For example, the fluid may enter the channel 102 flowing in a laminar fashion, and then alternatingly switch between clockwise and counter clockwise rotations as the fluid encounters consecutive, offset herringbone patterns. In some implementations, the number of chevrons per herringbone pattern and/or the number of groupings is configured to create a specific level of mixing over a given length of the device 100. In some implementations, the herringbone pattern does not alternate, but is constant along the duration of the flow channel. In some of these implementations the center of the herringbone patterns is in the center of the channel, while in other implementations the center of the pattern is off-center with respect to the channel.

As illustrated in FIGS. 4C and D, in some implementations, the mixing of a fluid is created with slanted ridges. Similar to the herringbone patter described above, in some implementations the slanted ridge pattern also creates a swirling rotation of the fluid that drives fluid from the bottom of the fluid flow channel towards the permeable membrane 103. In some implementations, the angle of the slanted ridge and the herringbone patter is between about 35 and about 55 degrees. In some implementations, the spacing between the ridges is between about 50 microns and about 100 microns, between about 100 microns and 150 microns, or between about 150 and about 200 microns. In some implementations, the spacing of the ridges is $2\pi/$(the width of the channel), such that the diameter of the induced rotation is less than the width or depth of the channel. In some implementations, the ridges of the above implementations are rounded.

In yet other implementations, the passive mixing elements 106 are designed to create vortices and other high and low pressure areas which drive the fluid towards the membrane 103. For example, FIGS. 4E and 4F, like the illustrative implementation of FIG. 3, include a plurality of ridges. In some implementations, the ridges are spaced between about 20 microns and about 50 microns, between about 50 microns and 100 microns or between about 100 microns and 500 microns.

In some implementations, the passive mixing elements can be, but are not limited to, posts, mounds, ramps, pits, cones or any combination thereof. FIGS. 4G-4J illustrate a possible post and mound implementation. In the implementation illustrated in FIGS. 4G and 4H, each row of posts is off set from the previous row. This causes the fluid to mix laterally in addition to driving fluid upwards. In other implementations, as illustrated in FIGS. 4I and 4J, the passive mixing elements are aligned with the passive mixing elements in the previous row.

Figure 5:
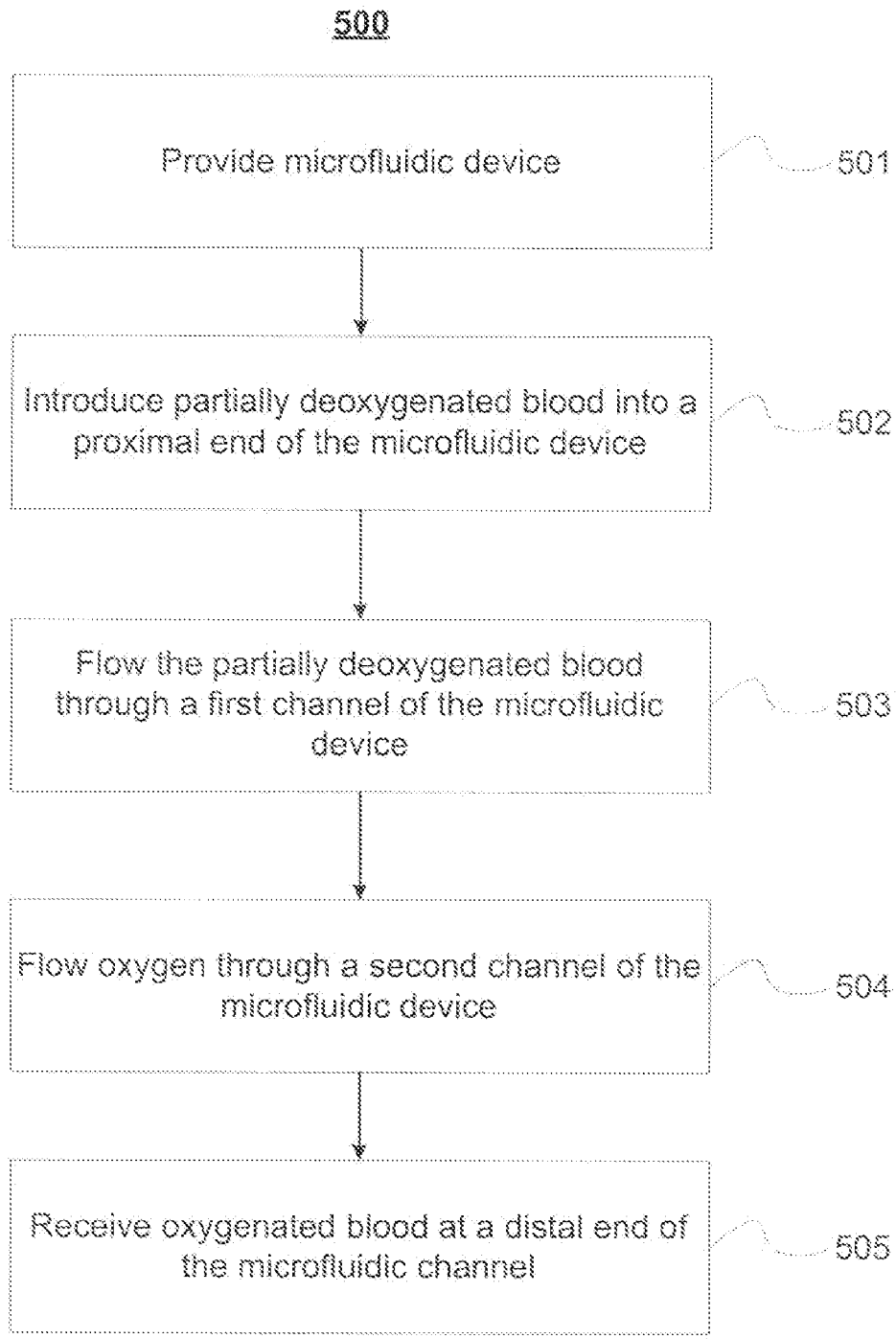
FIG. 5 is a flow chart of a method for oxygenating deoxygenated blood with a blood oxygenation device as depicted in FIG. 1, in accordance with an illustrative implementation of the present disclosure.

FIG. 5 is a flow chart of a method 500 for oxygenating blood with a microfluidic device. First, a microfluidic device is provided (step 501). Then, partially deoxygenated blood is introduced into a proximal end of the microfluidic device (step 502). The partially deoxygenated blood is flowed through a first channel of the microfluidic device (step 503), and oxygen is flowed through a second channel of the microfluidic device (step 504). Finally, oxygenated blood is collected from a distal end of the microfluidic device (step 505).

As set forth above, and referring to FIG. 1, the method 500 for oxygenating partially deoxygenated blood begins with providing a microfluidic device (step 501). In some implementations, the microfluidic device is similar to device 100 described above. In other implementations, the microfluidic device includes a plurality of oxygen channels and/or a plurality of blood flow channels. In yet other implementations, the microfluidic device is a array of devices similar to device 100. In some implementations, the device is configured to allow for about 500-1000 mL/min, about 1-4 L/min, or about 4-5 L/min of blood flow. In some implementations, the device is configured to transfer oxygen into the blood at a rate of about 160 to about 200 mL/min.

Next, the method 500 of oxygenating blood continues with the introduction of partially deoxygenated blood into a proximal end of the microfluidic device (step 502). In some implementations, the blood is directly collected form a patient and introduced into the device. For example, the device may be part of a heart-lung bypass system that oxygenates blood during surgery. In other implementations, the blood is collected, stored, and then oxygenated at a later time. For example, the blood may be collected during a blood drive and then oxygenated prior to being transfused into a patient. In some implementation, the blood is actively pumped through the device by an external pump, and in other implementations the blood is pumped through the device by the patient's heart.

The method 500 continues by flowing the partially deoxygenated blood through a first blood flow channel (step 503). As described above, the device includes at least one passive mixing element that inducing mixing within the channel as the blood travels the length of the device. In some implementations, the blood is thinned with a blood thinning agent such as the drug Coumadin or Heparin. In some implementations, the walls of the blood flow channels are coated with an anticoagulant.

Responsive to flowing blood through the first blood flow channel, the method 500 continues by flowing oxygen through a first oxygen flow channel (step 504). Referring to FIG. 1, the blood flow channel and oxygen flow channel are separated by a permeable membrane. Oxygen diffuses through the membrane, oxygenating the blood as it flows down the length of the channel. In some implementations, the blood is continually mixed within the channel by the passive mixing elements similar to those described above. In some implementations, the continual mixing allows a given volume of deoxygenated blood to be oxygenated more efficiently by continually exposing different red blood cells to the region near the membrane where oxygen diffusion can occur. In other implementations, the membrane is also porous to carbon dioxide, and the carbon dioxide initially within the deoxygenated blood diffuses into the oxygen flow channel. In yet other implementations, the oxygen and blood are flowed through the microfluidic device starting at different ends. For example, the blood may enter the device at a proximal end and the oxygen may enter the device at a distal end of the device.

The method 500 continues, with the collection of the oxygenated blood at a distal end of the microfluidic channel. In some implementations, the oxygenated blood is transfused directly back into the patient from which it was collected. In other implementations, the blood is collected and stored for later transfusion or experimentation.

What is claimed:

1. A microfluidic oxygenation device comprising:
   a first polymer layer defining a first oxygen flow channel therein;
   a second polymer layer defining a first blood flow channel therein, the first blood flow channel overlapping the first oxygen flow channel, and the first blood flow channel further comprising a plurality of passive mixing elements spaced sequentially along a length of a first wall of the first blood flow channel, wherein the plurality of passive mixing elements have a height or a depth less than about 30% of a height of the first blood flow channel and are configured to redistribute a fluid flowing through the first blood flow channel within the channel; and
   a membrane separating the first oxygen flow channel and the first blood flow channel at the overlapping portions of the channels, the membrane allowing communication between the first oxygen flow channel and the first blood flow channel.

2. The device of claim 1, wherein each of the plurality of passive mixing elements comprises one of a straight ridge, an angled ridge, a chevron canal, a dome, a cone, a pit or a post.

3. The device of claim 1, wherein a first fluid flows through the first oxygen flow channel and a second fluid flows through the first blood flow channel.

4. The device of claim 3, wherein the first fluid is oxygen and the second fluid is deoxygenated blood.

5. The device of claim 1, wherein the first wall of the first blood flow channel is the floor of the first blood flow channel.

6. The device of claim 1, wherein the height of the first blood flow channel is between about 10 and 100 microns.

7. The device of claim 1, wherein the membrane thickness is between about 10 and about 50 microns.

8. The device of claim 1, wherein the length of the first oxygen flow channel and the first blood flow channel is between about 1 mm and about 50 mm.

9. The device of claim 1, where the width of the first blood flow channel is between about 100 microns and 200 microns.

10. The device of claim 1, wherein the membrane is permeable to oxygen and carbon dioxide.

11. The device of claim 1, wherein the walls of the first blood flow channel are coated with an anticoagulant.

12. The device of claim 1, wherein the device includes a second blood flow channel separated from the first oxygen flow channel by a second permeable membrane.

13. A method for oxygenating deoxygenated blood, the method comprising:
    providing a microfluidic device comprising a first polymer layer defining a first oxygen flow channel; a second polymer layer defining a first blood flow channel, the first blood flow channel further comprising a plurality of passive mixing elements spaced sequentially along a length of a surface of the first blood flow channel, wherein the plurality of passive mixing elements have a height or a depth less than about 30% of a height of the first blow flow channel; and a membrane separating the first oxygen flow channel and the first blood flow channel, the membrane allowing communication between the first oxygen flow channel and the first blood flow channel;
    introducing partially deoxygenated blood into a proximal end of the microfluidic device;
    flowing oxygen through the first oxygen flow channel;
    flowing the partially deoxygenated blood through the first blood flow channel; and
    receiving oxygenated blood at a distal end of the microfluidic device.

14. The method of claim 13, further comprising:
    collecting partially deoxygenated blood from a patient;
    flowing the partially deoxygenated blood through the first blood flow channel to reoxygenate the blood; and
    returning the reoxygenated blood to the patient.

15. The method of claim 14, further comprising removing carbon dioxide from the partially deoxygenated blood as the partially deoxygenated blood flows through the first blood flow channel.

16. The method of claim 13, further comprising flowing oxygen through the first oxygen flow channel from a first direction.

17. The method of claim 13, further comprising flowing blood through the first blood flow channel in a second direction opposite to the first direction.

18. The method of claim 13, further comprising flowing the blood through the first blood flow channel at 4-5 L/min.

19. The method of claim 13, further comprising transferring oxygen into the blood at a rate of about 150-200 mL/min.

* * * * *